United States Patent

Joullié et al.

[11] 4,065,575
[45] Dec. 27, 1977

[54] 3-AMINOMETHYL DERIVATIVES OF 4-CHROMANONE

[75] Inventors: Maurice Joullié, Saint-Germain-en-Laye; Gabriel Maillard, Paris; Lucien Lakah, Paris; Christian Jean Marie Warolin, Paris, all of France

[73] Assignee: Joullié International, Neuilly-sur-Seine, France

[21] Appl. No.: 659,708

[22] Filed: Feb. 20, 1976

[30] Foreign Application Priority Data

Feb. 20, 1975 France .................................. 75.05298

[51] Int. Cl.² .................... A61K 31/35; C07D 311/02
[52] U.S. Cl. .................................. 424/283; 260/345.2
[58] Field of Search ...................... 260/345.2; 424/283

[56] References Cited

U.S. PATENT DOCUMENTS 2,621,189  12/1952  Wiley .............................. 260/345.2
3,706,764  12/1972  Nakanishi et al. .............. 260/345.2

OTHER PUBLICATIONS

Wiley, J. Am. Chem. Soc., 73, 4205 (1951).

*Primary Examiner*—Nicky Chan
*Attorney, Agent, or Firm*—Stevens, Davis, Miller & Mosher

[57] ABSTRACT

4-Chromanone derivatives of the formula:

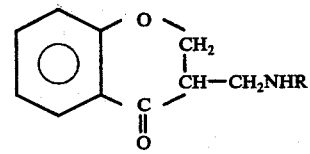

wherein R represents alkyl of 1 through 6 carbon atoms or alkoxyalkyl of 2 through 6 carbon atoms, are new compounds possessing pharmacological properties and are useful inter alia as vasodilators.

2 Claims, No Drawings

3-AMINOMETHYL DERIVATIVES OF 4-CHROMANONE

The present invention relates to new derivatives of 4-chromanone, to a process for their preparation and pharmaceutical compositions containing them. The new 4-chromanone derivatives of the invention are those compounds which carry a substituted-aminomethyl group on the 3-position carbon atom and possess useful pharmacological activity inter alia as vasodilators.

Certain derivatives of 4-chromanone carrying an amine substituent on the 3-position carbon atom are known; for example, 4-chromanone compounds which carry a dimethylaminomethyl or piperidinomethyl radical have already been described by Couturier, Bull. Soc. Chim. Fr. 12, 4777–80 (1972), and Whiley, J. Chem. Soc. 73, 4205, respectively.

The 4-chromanone derivatives of the present invention are those compounds of the general formula:

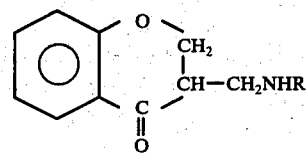

wherein R represents an alkyl radical of 1 to 6 carbon atoms or an alkoxyalkyl group of 2 to 6 carbon atoms, and pharmaceutically-acceptable inorganic and organic acid addition salts thereof, especially the hydrochlorides.

Preferred compounds of the invention are those of general formula I wherein R represents the propyl, butyl or pentyl radical or a 2-methoxyethyl, 3-methoxypropyl or 4-methoxybutyl group. Of outstanding importance is 3-(2-methoxyethylaminomethyl)-4-chromanone.

According to a feature of the invention, the 4-chromanone derivatives of general formula I are prepared by application of the Mannich reaction, in accordance with the method described by A. B. SEN and S. L. ARORA (J. Ind. Chem. 35, 95, 1958), to 4-chromanone.

For this purpose, a mixture of 4-chromanone, paraformaldehyde and the hydrochloride of an amine $RNH_2$ (wherein R is as hereinbefore defined) in an organic solvent is heated at the reflux temperature, the three reactants being present in equimolecular amounts. The reaction mixture is then acidified with a few ccs. of a solution of dry hydrogen chloride in anhydrous benzene to give the hydrochloride of the Mannich base. In general, the hydrochloride separates out in the form of crystals. The product is filtered off and recrystallised from a suitable solvent.

The reaction solvent is preferably anhydrous dry benzene or a polar solvent such as an alcohol, for example ethanol, isopropanol or isoamyl alcohol. The heating time ranges from 3 to 11 hours at a temperature of from 60° C. to 100° C.

4-Chromanone is synthesised by cyclisation of phenoxypropionic acid, in accordance with the method described by W. E. PARHAM (J.A.C.S. 84, 813–816, 1962), or by that of D. HUCKLE (J. Med. Chem. 12, 1969) from propiolactone and phenol.

Acid addition salts of the 4-chromanone derivatives of general formula I can be prepared by methods known per se, e.g. by treatment of the bases (liberated from the hydrochlorides obtained as described hereinbefore by methods known per se) with an inorganic or organic acid in the presence of a solvent such as diethyl ether.

By the term "methods known per se" as used in this specification is meant methods heretofore used or described in the literature.

The Examples which follow illustrate the 4-chromanone derivatives of the present invention. The process of preparation used is that hereinbefore described.

EXAMPLE 1

3-(n-Propylaminomethyl)-4-chromanone hydrochloride (hereinafter referred to as LJ 1048)

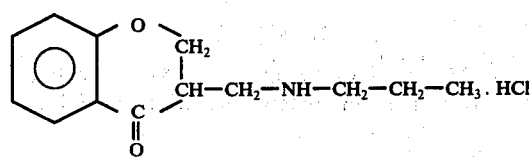

Recrystallised from ethanol and then from dioxan.
White crystals, melting point: 180° C. (Tottoli).
Yield: 25%

| Analysis: Calculated for $C_{13}H_{18}O_2N\ Cl = 255.7$ | | | |
|---|---|---|---|
| C% | 61.05 | found | 61.15 |
| H% | 7.09 | | 7.17 |
| N% | 5.47 | | 5.60 |

EXAMPLE 2

3-(n-Butylaminomethyl)-4-chromanone hydrochloride (hereinafter referred to as LJ 1049)

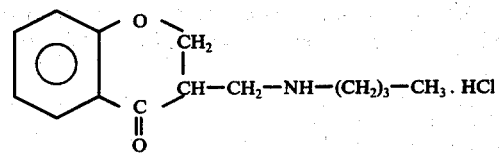

Recrystallised from ethanol and then from tetrahydrofuran
White crystals, melting point: 166° C. (Tottoli).
Yield: 45%

| Analysis: calculated for $C_{14}H_{20}O_2\ N\ Cl = 269.7$ | | | |
|---|---|---|---|
| C% | 62.33 | found | 62.11 |
| H% | 7.47 | | 7.51 |
| N% | 5.19 | | 5.35 |

EXAMPLE 3

3-(n-Pentylaminomethyl)-4-chromanone hydrochloride (hereinafter referred to as LJ 1046)

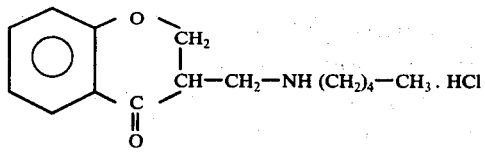

Recrystallised from ethanol.
Melting point: 170° C. (Tottoli)
Yield: 25%

| Analysis: calculated for $C_{15}H_{22}O_2 N Cl = 233.5$ | | | |
|---|---|---|---|
| C% | 63.48 | found | 63.22 |
| H% | 7.80 |  | 7.91 |
| N% | 4.93 |  | 4.96 |

EXAMPLE 4

3-(2-Methoxyethylaminomethyl)-4-chromanone hydrochloride (hereinafter referred to as LJ 1052)

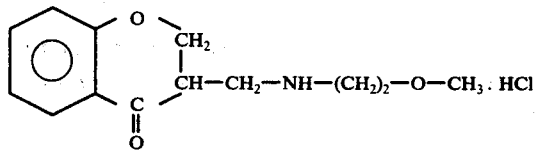

Recrystallised from ethanol and then from ethyl acetate.
White crystals, melting point: 120°-121° C. (Tottoli)
Yield: 31%

| Analysis: calculated for $C_{13}H_{18}O_3 N Cl = 271.74$ | | | |
|---|---|---|---|
| C% | 57.46 | found | 57.45 |
| H% | 6.67 |  | 6.67 |
| N% | 5.15 |  | 5.12 |

EXAMPLE 5

3-(3-Methoxy-n-propylaminomethyl)-4-chromanone hydrochloride (hereinafter referred to as LJ 1051)

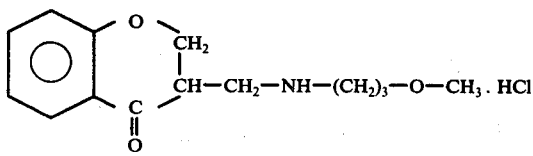

Purification: The crude hydrochloride is dissolved in water, the solution is rendered alkaline with dilute ammonium hydroxide and the base is extracted with diethyl ether. The ether phase is washed with water and dried.

The hydrochloride is formed again by adding a dry solution of hydrogen chloride in diethyl ether.
White crystals, melting point: 147° C.
Yield: 18%

| Analysis: calculated for $C_{14}H_{20}O_3 N Cl = 285.77$ | | | |
|---|---|---|---|
| C% | 58.4 | found | 58.70 |
| H% | 7.04 |  | 7.17 |
| N% | 4.90 |  | 4.70 |

EXAMPLE 6

3-(4-Methoxy-n-butylaminomethyl)-4-chromanone hydrochloride (hereinafter referred to as LJ 1053)

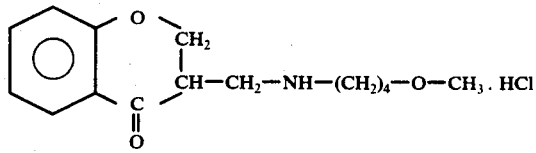

The 4-methoxybutylamine [$NH_2$—$(CH_2)_4$—O—$CH_3$] was prepared according to Schlink, Ber. 32, 948 (1899), and chloromethoxypropane, the starting material for the reaction, was prepared according to Haworth and Perkin, J. Chem. Soc. 65, 596 (1894).

3-(4-Methoxy-n-butylaminomethyl)-4-chromanone hydrochloride is chromatographed on a column of Merck silica, with the desired product passing into the ethanol fraction.

White crystals, melting point: 139° C.
Yield: 23%

| Analysis: calculated for $C_{15}H_{22}O_3 N Cl = 299.79$ | | | |
|---|---|---|---|
| C% | 60.09 | found | 59.98 |
| H% | 7.39 |  | 7.45 |
| N% | 4.67 |  | 4.62 |

The thin layer chromatography is carried out on Gelman Saf glass fibres, using 4 parts of xylene and 1 part of acetone (v/v) as the solvent system.
Developers: U.V. and iodine.

The compounds of the invention were subjected to pharmacological tests.

I. ACUTE TOXICITY IN MICE

The study is carried out on batches of 5 Swiss female mice of the NMRI Han. strain. The products are administered either intravenously (into the caudal vein) in solution in a 9 g. sodium chloride solution, or orally (probang) in suspension in a 10% solution of gum arabic.

The animals are observed for the 15 days following the administration of the products.

The LD 50 values are calculated by the method of Karber and Behrens (Arch. Exp. Pathol. Pharm. 177, 1935, page 379).

TABLE No. I

| | Acute toxicity in mice | |
|---|---|---|
| | LD 50 in mg./kg. | |
| Products | Intravenous administration | Oral administration |
| LJ 1046 | 18 | 237 |
| LJ 1048 | 36 | 362 |
| LJ 1049 | 24 | 262 |
| LJ 1051 | 33 | 475 |
| LJ 1052 | 47 | 475 |
| LJ 1053 | 38 | 285 |

LD 50 = 50% lethal dose.

II. PHARMACODYNAMIC STUDY

1. Action on the smooth intestinal fibre

The experiments are carried out in accordance with the method of Magnus R. (Arch. ges. Physiol. 1904, 102, 123) on the isolated duodenum of a rat, surviving in oxygenated Tyrode liquid and kept at 38° C. The tonus and the pendular movements of the duodenum were recorded by means of a strain gauge on an electronic polygraph.

The inherent action of the products, and the antagonism exerted against the musculotropic contraction-inducing action of barium chloride was examined. Papaverine is used as the reference substance.

All the products studied have an inherent relaxing action. The concentrations which inhibit, to the extent of 50%, the contraction-inducing action of barium chloride are indicated in Table No. II and show that the musculotropic spasmolytic action of the six products studied is equivalent to, or greater than, that of papaverine. LJ 1046 proved the most active.

TABLE No. II

| Products | Musculotropic spasmolytic action on the isolated duodenum of a rat 50% inhibitory concentrations |
|---|---|
| LJ 1046 | $2 \times 10^{-7}$ to $5 \times 10^{-7}$ |
| LJ 1048 | $5 \times 10^{-7}$ |
| LJ 1049 | $5 \times 10^{-7}$ |
| LJ 1051 | $2 \times 10^{-6}$ |
| LJ 1052 | $5 \times 10^{-6}$ |
| LJ 1053 | $5 \times 10^{-7}$ to $2 \times 10^{-6}$ |
| Papaverine | $2 \times 10^{-6}$ to $5 \times 10^{-6}$ |

2. Action on the peripheral vasomotoricity

The action on the peripheral vasomotoricity was studied by the technique of Swetschnikow (Arch. f. ges. Physiol. 1914, 157, 471) and Pissemski (Pfluger's Arch. 1914, 156, 426) by perfusing the isolated auricle of a rabbit through the central artery with Tyrode liquid to which naphthazoline (concentration $10^{-5}$) has been added to induce a prior vasoconstriction. The flow rate of the liquid issuing from the veins is recorded by electronic contact on a polygraph. The products to be studied are injected at increasing doses into the perfusion tube and their actions are compared to that of isoxsuprine used as the reference substance.

The results, collected in Table No. III, are expressed in the maximum percentage increase of the flow rate at the various doses used.

All the products exhibit a peripheral vasodilatory action.

Compound LJ 1048 proved to have a low activity.

For compound LF 1046, the maximum increases in the flow rate never exceed 100%; the duration of the effects varies between 15 and 30 minutes at the highest doses.

For the compounds LJ 1049, 1051, 1052 and 1053, the vasodilatory action is great. At the highest doses, the duration of the action is equal to or greater than 30 minutes.

The compounds LJ 1052 and LJ 1053 are as active as isoxsuprine and the effects of LJ 1052 are great even at very low doses.

TABLE No. III

| | Action on the vasomotoricity of an isolated and perfused auricle of a rabbit | | | | | | |
|---|---|---|---|---|---|---|---|
| Doses in μg. | Maximum variations in the flow rate, in % | | | | | | |
| | LJ 1046 | LJ 1048 | LJ 1049 | LJ 1051 | LJ 1052 | LJ 1053 | Isoxsuprine |
| 0.1 | +38% | +22% | +36% | 0 | +79% | +23% | +38% |
| 1 | +29% | +33% | +36% | +36% | +77% | +92% | +61% |
| 10 | +61% | +33% | +115% | +100% | +100% | +133% | +117% |
| 100 | +77% | +29% | +138% | 30 145% | +150% | +183% | +175% |

3. Action on the reactivity of the autonomous nervous system a. In normal rats

The operation is carried out on a male rat (weight 300 to 400 g.) anaesthetised with ethyl carbamate (1.25 g./kg. administered intraperitoneally), and the mean carotid arterial pressure of the rat is recorded by means of a Racia variable inductance sensor connected to a polygraph.

The products are injected by means of a cannula placed in the vein of the penis. The effects of adrenaline (2 μg./kg. administered intravenously), of noradrenaline (2 μg./kg. administered intravenously), of acetylcholine (5 μg./kg. administered intravenously) and of isoprenaline (2 μg./kg. administered intravenously) on the blood pressure are determined before and after injection of the products under test, and the inherent effects of these products on the arterial pressure are also recorded.

The results obtained after injection of doses corresponding to 1/10 of the intravenous LD 50 in mice show that:

The various products all produce substantial ($-40$ to $-50\%$) and lasting reductions in the arterial pressure.

They completely cancel out the hypertensive effects of adrenaline, and markedly reduce those of noradrenaline, and thus possess a blocking action on the α-adrenergic receptors.

They have no action on the hypotensive effects of acetylcholine and of isoprenaline.

b. In amyeliated rats

The α-sympatholytic effects of LJ 1052 and LJ 1053 are compared with those of isoxsuprine in amyeliated rats which have been prepared by a method derived from those of Shipley and Tilden (Proc. soc. Exp. Biol. Med. 1947, 64, 453-455) and of Gillespie and Muir (Br. J. Pharmac. Chemother. 1967, 30, 78-87).

The effects on the blood pressure of electrical stimulation of the thoracolumbar sympathic nerve (rectangular signals = voltage 20 to 40 volts; width 2 m. sec; frequency 10 secs.; duration 5 to 10 secs.) and of injections of adrenaline (1.25 to 2.5 μg./kg.) and of noradrenaline (1.25 to 2.5 μg./kg.) are determined before and after injection of the products tested.

The results obtained are summarised in Table No. IV and show that LJ 1052 is less α-sympatholytic than LJ 1053 and isoxsuprine used at the same doses (the intravenous LD 50 in mice, of these three products, being practically identical).

TABLE No. IV.

Comparison of the α-sympatholytic effects of LJ 1052, LJ 1053 and isoxsuprine on amyeliated rats

| Products | Doses in g./kg. | % variation of the hypertensive effects obtained with: | | |
|---|---|---|---|---|
| | | Electrical stimulation | Adrenaline | Noradrenaline |
| LJ 1052 | 50 | 0 | −15% | −11% |
| | 100 | 0 | −28% | −12% |
| | 500 | −20% | −77% | −38% |
| | 2,500 | −80% | −77% | −50% |
| Isoxsuprine | 50 | −27% | −69% | −36% |
| | 100 | −25% | −75% | −44% |
| | 500 | −66% | −100% | −67% |
| LJ 1053 | 50 | −11% | −18% | −12% |
| | 100 | −55% | −47% | −41% |

4. Cardiovascular action in dogs

Male Beagle dogs weighing 9 to 12 kg. were anaesthetised by intrasaphenous injection of a 2% solution of chloralose in physiological solution, at a dose of 100 mg./kg.

The anaesthesia is maintained by slow perfusion of 5% pentobarbital (1.2 ml./hour).

The animals are tracheotomised and placed under assisted respiration by means of a Bird respirator. Their oxygenation and their acid-base equilibrium are controlled by determination of the pH, the $pCO_2$ and the $pO_2$ on blood samples taken from a collateral of the brachial artery (pH/gas analyser for blood, IL model 213/227).

The different parameters are recorded on a polygraph.

The results obtained with the various products studied at low doses, that is to say at therapeutic doses, are summarised in Table No. V. They demonstrate the following facts:

All the products more or less lastingly reduce the mean arterial pressure (the diastolic pressure is reduced whilst the systolic pressure is increased, and hence the differential is widened).

They reduce the left ventricular pressure and in general increase the dLVP/dt, which indirectly indicates an increase in the cardiac contractile force.

They increase the cardiac frequency.

They more or less intensely and lastingly increase the femoral flow rate. In this respect, LJ 1052 appears to be the most interesting product, having an activity comparable to that of isoxsuprine, which confirms the results obtained on the isolated auricle of a rabbit.

These modifications of the cardiovascular parameters are the reflection of a stimulating action on the β1-cardiac receptors and β2-vascular receptors.

TABLE No. V

Cardiovascular actions at low doses in dogs

| Products | Doses in mg./kg. administered intravenously; fractions of the LD 50 | Systolic AP % | Systolic AP D | Diastolic AP % | Diastolic AP D | Mean AP % | Mean AP D |
|---|---|---|---|---|---|---|---|
| LJ 1046 | 0.36 (1/50 LD 50) | — | | — | | −36% | >20 mins. |
| LJ 1048 | 0.7 (1/50 LD 50) | — | | — | | −38% | >60 mins. |
| LJ 1049 | 0.5 (1/50 LD 50) | — | | — | | −15% | 10 mins. |
| LJ 1051 | 0.6 (1/50 LD 50) | — | | — | | −21% | >50 mins. |
| LJ 1052 | 0.04 (1/1,000 LD 50) | +13% | 30 mins. | −29% | 2 mins. | −25% | 2 mins. |
| LJ 1053 | 0.04 (1/1,000 LD 50) | +23% | 15 mins. | −60% | 5 mins. | −45% | 5 mins. |
| Isoxsuprine | 0.04 (1/1,000 LD 50) | +13% | 10 mins. | −62% | 20 mins. | −50% | 20 mins. |

| Products | Doses in mg./kg. administered intravenously; fractions of the LD 50 | LVP % | LVP D | dLVP/dt % | dLVP/dt D | Hb % | Hb D | FF % | FF D |
|---|---|---|---|---|---|---|---|---|---|
| LJ 1045 | 0.36 (1/50 LD 50) | −20% | >20 mins. | +43% | >20 mins. | +30% | >20 mins. | +100% | >20 mins. |
| LJ 1043 | 0.7 (1/50 LD 50) | −21% | 30 mins. | +28% | 60 mins. | +33% | >60 mins. | — | — |
| LJ 1049 | 0.5 (1/50 LD 50) | −19% | 50 mins. | −10% then +20% | 10 mins. | +21% | 40 mins. | +34% | 2 mins. |
| LJ 1051 | 0.6 (1/50 LD 50) | −30% | >50 mins. | −60% | >50 mins. | +20% then −16% | 3 mins. 40 mins. | — | — |
| LJ 1052 | 0.04 (1/1,000 LD 50) | +9% | 25 mins. | +34% | 30 mins. | +14% | 25 mins. | +91% | 30 mins. |
| LJ 1053 | 0.04 (1/1,000 LD 50) | −17% then +7% | >10 mins. | −12% then +25% | >10 mins. | +23% | >30 mins. | +104% | 3 mins. |
| Isoxsuprine | 0.04 (1/1,000 LD 50) | −22% | 5 mins. | −18% then | | +13% | 25 mins. | +63% | 30 mins. |

TABLE No. V-continued

| Cardiovascular actions at low doses in dogs | |
|---|---|
| +12% | 5 mins |

% = Maximum per cent variation.
D = Duration of action, that is to say time required to return to normal.
AP = Arterial pressure.
LVP = Left ventricular pressure.
dLVP/dt = Maximum rate of increase of the LVP.
Hb = Heart beat.
FF = Mean flow rate of the femoral artery.

The 4-chromanone derivatives of the invention exhibit the following:

A musculotropic spasmolytic activity comparable to that of papaverine;

a large peripheral vasodilatory action which is long-lasting for certain representatives of the series;

a more or less long-lasting hypotensive action at low doses;

a cardiac and vascular β-stimulant action which is shown clearly at a low dose and is in equilibrium with an adrenolytic action which overtakes the β-stimulant action and becomes preponderant at high doses.

The most valuable product of the series is LJ 1052, the cardiovascular action of which is comparable to or even greater than that of isoxsuprine.

Furthermore, LJ 1052 possesses marked anti-platelet-aggregation properties in vitro.

In the ADP aggregation test, LJ 1052 proved to be almost as active as adenosine and in the collagen aggregation test its anti-aggregation action is similar to that of aspirin.

The therapeutic indications for the derivatives of the invention, in particular LJ 1052, are essentially circulatory disturbances which require an increase in the blood flow rate in ischaemic zones.

The following may be distinguished:

Arterites of the lower members, of any origin;

peripheral circulatory insufficiencies:

Vasomotor disturbances of the extremities, such as Raynaud disease, acrocyanosis and acroparaesthesia, vascular disturbances associated with diabetes, arterial sclerosis, thrombo-embolic occurrences (anti-platelet-aggregation activity) and disturbances resulting from thrombo-embolic disorders.

Cerebral circulatory insufficiencies:

Cerebral vascular disturbances and cerebral ischaemia, vascular disturbances in ORL and in ophthalmology.

Finally, the high spasmolytic activity of papaverine associated with the α-spasmolytic activity of these derivatives, in particular LJ 1052, results in their having valuable relaxing properties on the uterus, especially in spasmodic dismenorrhoeas.

The daily therapeutic dose administered will be about 0.4 mg./kg., representing 20 to 30 mg. for an adult. The daily posology for an adult will be, for example, from 2 to 3 tablets containing 10 mg., or the contents of 1 or 2 ampoules containing 5 mg. and injected intramuscularly.

The present invention includes within its scope pharmaceutical compositions which comprise, as active ingredient, a 4-chromanone derivative of general formula I, or a non-toxic acid addition salt thereof, in association with a pharmaceutically-acceptable carrier or diluent. The compositions can be presented for therapeutic use in a variety of forms such as tablets, gelatine-coated pills and injectable solutions.

It is particularly desirable to use forms which have a prolonged action and gradually liberate the active ingredient for therapeutic use over long periods. For example, a complex of LJ 1052 (in the form of the base) and a polyanionic resin (of the polystyrene-polysulphonic acid type) makes it possible to space out the administrations at intervals of 12 hours.

Thus, the galenical forms described in following Example 7 have been produced.

| | |
|---|---|
| Tablets: | |
| LJ 1052 | 10 mg. |
| excipient, q.s.p. for 1 tablet of | 200 mg. |
| Gelatine-coated pills: | |
| LJ 1052 | 10 mg. |
| talc | 5 mg. |
| lactose | 85 mg. |
| Injectable solution: | |
| LJ 1052 | 5 mg. |
| water for an injectable preparation | 1 ml. |

We claim:
1. A method of providing a vasodilating effect to a subject requiring a vasodilating effect which comprises administering to said subject a vasodilating effective amount of a compound of the formula:

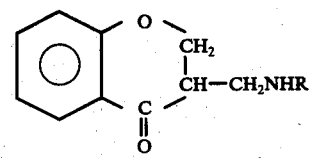

wherein R is alkyl of 1 through 6 carbon atoms or alkoxyalkyl of 2 through 6 carbon atoms.

2. The method of claim 1 wherein said compound is 3- (2-methoxyethylaminomethyl)-4-chromanone.